United States Patent [19]

Tapper

[11] 4,211,222
[45] Jul. 8, 1980

[54] IONTOPHORETIC BURN-PROTECTION METHOD

[76] Inventor: Robert Tapper, 175 Acari Dr., Los Angeles, Calif. 90012

[21] Appl. No.: 940,777

[22] Filed: Sep. 8, 1978

Related U.S. Application Data

[63] Continuation-in-part of Ser. No. 717,791, Aug. 25, 1976, abandoned.

[51] Int. Cl.² ............................................. A61N 1/30
[52] U.S. Cl. .............................. 128/207.21; 128/803
[58] Field of Search .............. 128/803, 783, 791–793, 128/795, 796, 798, 802, 172.1, 419 R

[56] References Cited

U.S. PATENT DOCUMENTS

| | | | |
|---|---|---|---|
| 2,590,876 | 4/1952 | Landauer | 128/803 |
| 2,784,715 | 3/1957 | Kestler | 128/172.1 |
| 3,289,671 | 12/1966 | Troutman et al. | 128/172.1 X |
| 3,386,445 | 6/1968 | McDonald | 128/798 |
| 3,474,775 | 10/1969 | Johnson | 128/639 |
| 3,817,252 | 6/1974 | Maurer | 128/798 |
| 3,848,600 | 11/1974 | Patrick, Jr. et al. | 128/783 X |

FOREIGN PATENT DOCUMENTS 614552 12/1948 United Kingdom ...................... 128/783

OTHER PUBLICATIONS

Levit, "Simple Device . . . Iontophoresis," Archives of Dermatology, vol. 98, Nov. 1968, pp. 505–507.

*Primary Examiner*—Lee S. Cohen
*Attorney, Agent, or Firm*—Fulwider, Patton, Rieber, Lee & Utecht

[57] ABSTRACT

A method, and typically a pair of treatment electrodes energized at opposite electrical polarity, is provided for applying electricity to the human body. At least the area of the negative electrode in contact with the skin is covered with felt-like material, preferably moistened, and having a thickness in excess of three millimeters. Compliance with a current-time limitation according to the method essentially avoids iontophoretic burns. Electively, this negative electrode structure allows increasing the size of the positive electrode, permitting a larger treatment current with reduced discomfort. Intermingled positive and negative electrodes may be used.

4 Claims, 5 Drawing Figures

IONTOPHORETIC BURN-PROTECTION METHOD

BACKGROUND OF THE INVENTION

This is a continuation-in-part of prior application Ser. No. 717,791, filed on Aug. 25, 1976, now abandoned. This invention pertains to plural electrodes for application to a living subject having skin, to accomplish effects related to the passage of electric current.

Around the turn of the century the art disclosed a plethora of electrode types for applying "electric treatments" to the human body. The electrodes were normally placed upon the body in relation to the position of an organ to be treated.

These "electric treatments" encompassed a wide range of applications. For example, galvanic (direct current) treatments have been popular in the past for their polar effects on ionized molecules, causing the ionized molecules to be driven through the skin, usually superficially. This phenomenon is known as iontophoresis or ion transfer, and it has been employed for the introduction of medicants, or even simply moisture, into the skin of a patient.

More specifically, some ions of zinc and copper can be employed in the treatment of some skin infections, and chlorine ions have been employed for the loosening of superficial scars. Further, vasodilating drugs can be used in rheumatic and peripheral vascular affections, and skin anesthesia can be produced by iontophoresis of local anesthetic drugs. It has been suggested that application of direct current to carefully selected areas of a living animal can produce anesthetic effects. (See Limoge, *An Introduction to Electroanesthesia*, 1975, University Park Press).

In general, the electrodes were disclosed merely as structures and were not related to any undersirable side-effects the electric current might have upon the skin. An example is the U.S. Pat. No. 562,765, issued in 1896 to Horton, Jr. The usual objective was merely to decrease the contact resistance to the skin.

F. Levitt in "Archives of Dermatology", Vol. 98 No. 5, November 1968, reports on pps. 505-7 the production of long term anhidrosis by electric treatment of the feet, or hands. However, he disclosed only the use of a "a two inch square of sheet lead" as an electrode. This is "placed in a shallow pan containing enough water to just cover the palm or soles"; there being one electrode and one pan for each palm or sole. His test results indicate that the treatment inhibits perspiration (sweat) where the electric current is provided.

Although the above mentioned iontophoretic treatments have been found to be effective, using known electrodes in these direct current application frequently results in iontophoretic burns to the patient, generally at the negative electrode. These burns are not caused by elevated temperature but by a spontaneous effect of the electric current on the skin. These burns require a relatively long time to heal, and can result in formation of unsightly and highly undesirable scar tissue.

A paper by Leeming and Howland in the "Journal of the American Medical Association", Vol. 214, No. 9, Nov. 30, 1970, recites instances of burns but does not present means for preventing such trauma. This undesirable effect of iontophoretic treatment has resulted in a less than enthusiastic reception of iontophoretic techniques by the medical community in spite of the great and varied advantages to be realized through their use and development.

Accordingly, there has existed a need for a convenient and effective method for preventing iontopheric burns during the application of electrical energy to the skin of a human body. As will become apparent from the following, the present invention satisfies that need.

SUMMARY OF THE INVENTION

A means for applying electrical energy topically to the skin of the human body is provided by which undesired side-effects are greatly minimized and may be eliminated.

The electrode configuration of the invention includes two conductive areas to which opposite polarity of electric current is supplied and which may be relatively adjacent. When the electrodes are adjacent the electric current does not pass through or near electro-sensitive organs, such as the heart.

Although the present method of preventing iontophoretic burns will be described as used in connection with an electrical treatment for inhibiting perspiration, it will be understood that this method is equally well suited for use with other electrical treatments, such as the examples described above.

One side-effect that is substantially eliminated by the electrode structure of this invention is the iontophoretic burn. This is because of the interposition of relatively thick porous and preferably moistened material between the negative electrode and the skin.

Another side-effect that is reduced is pain or tingling due to the passage of current. This is brought about by increasing the area of the positive electrode.

An alternate embodiment utilizes intermingled negative and positive electrodes of small size, all having porous material.

DESCRIPTION OF THE PREFERRED EMBODIMENTS

Figure 1:
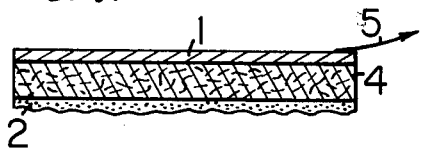
FIG. 1 is a sectional elevation, at 1—1 in FIG. 2, of a conductive electrode, the porous intervenor, and the skin to be treated.

In FIG. 1 numeral 1 indicates a conductive electrode. This may be flexible or rigid and is typically fabricated of metal, of which stainless steel and aluminum are examples.

The skin is represented by epidermis 2. This has been simply shown. The physiological detail of the epidermis is shown in a drawing on page 840, Vol 16, 15th Edition, copyright 1974 of the "Encyclopedia Britannica".

Porous intervenor material 4 is typically in loose electrical contact to the under side of electrode 1 so that it can be changed and discarded after each use.

A suitable material 4 is a type of felt that can be obtained commercially. While the thickness stipulated as principal in this invention is not commonly available, it can be obtained in special order. A quality control specification for this material is that it be free of tramp metal.

A thickness greater than 3 millimeters may be chosen if a greater value of the current times the time-of-treatment factor is desired.

Figure 2:
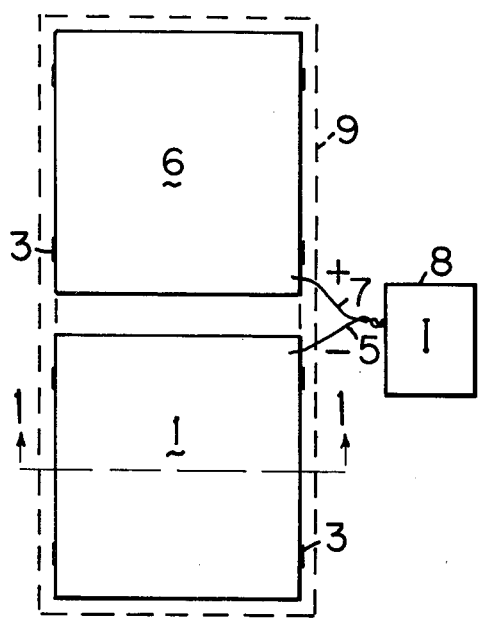
FIG. 2 is an illustrative plan view of a pair of electrodes and of the remainder of the system.
Figure 3:
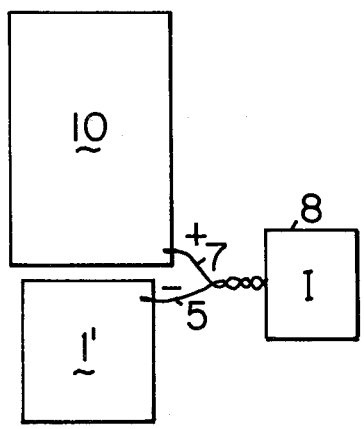
FIG. 3 is an alternate embodiment in which one electrode is larger than the other.

Flexible electrical condutor 5 is conductively connected to electrode 1. Electrode 1 may take the form of a snap fastener as well as a metallic plate or a conductive plastic such as silicone. Two examples of electrode arrangements are illustrated in FIGS. 2 and 3. In the view of FIG. 2 the negative electrode 1 is seen. Porous material 4 is underneath the same.

Second electrode 6 is shown adjacent to electrode 1, with a separation between the two of the order of a fraction of one to a few centimeters, typically. Positive electrode 6, connected by conductor 7 to a source 8 of electric current, may be a simple metallic electrode, with or without the thick porous intervenor 4.

Source 8 may be merely a source of direct current, such as a battery. The current normally required is within the range of from a fraction of a milliampere to twenty milliamperes. A known adjustable resistor may be included within source 8 to allow the user to obtain the proper current for any process.

For inhibiting perspiration a current density on the positive electrode of from 1/20 to perhaps $\frac{1}{2}$ milliampere per square centimeter is desired. Naturally, the actual current density and treatment duration employed in any of the above mentioned applications of this invention should be chosen to accomodate the particular case at hand. Accordingly, the actual values mentioned herein are offered as an example of one of the treatments which can employ the method of this invention.

Source 8 may also be a known "constant current source", having the same specifications as above and a control to allow the user to select the desired constant value of current. Another feature of a suggested unit would limit the maximum current that is applied.

The source of current may also have other forms, including unidirectional pulses or varying current, but not alternating current of commonly used frequencies, nor radio frequency current.

The arrangement of electrodes 1 and 6 may take many forms, depending upon the area that is to be treated and the choice of the designer. These electrodes may be attached to a non-conductive frame, which is shown dotted at 9 in FIG. 2. This is convenient for inhibiting perspiration on a hand or a foot.

Alternatively, positive electrode 6 may be placed on the palm of a hand for inhibiting perspiration there, and the negative electrode may be placed on the back of the hand, or on the wrist.

Connective means 3 attach electrodes 1 and 6 to frame 9.

Of course, the negative electrode may be placed elsewhere, such as in combination with the positive electrode within gloves for a hand or hands. The positive electrode is positioned to inhibit perspiration and the negative electrode is positioned adjacently for the current return. Similar arrangements are possible in stockings for the feet. Nominal pressure between the electrodes and the skin can thereby be maintained in any position.

For inhibiting underarm perspiration the positive electrode, at least, can be curved to fit under the armpit. The negative electrode may be located nearby, or the positive and negative electrodes can each occupy one-half of the axilla area, with an insulative separator between.

In FIG. 3, elements 5, 7, and 8 are as before. However, positive electrode 10 has a relatively large area and negative electrode 1' has a relatively small area. The positive electrode is rectangular, rather than square, as before. The electrode may have almost any shape when secondary considerations so require.

The configuration shown is useful for inhibiting perspiration of the hand. Electrode 10 is placed upon the palm of the hand and electrode 1' is placed upon the fingers of the same hand.

In the practice of perspiration inhibition and similar treatments it has been found that iontophoretic burn is associated with the means of the prior art at the current densities required to produce the desired result. Our investigation isolated the burn phenomenon to the negative electrode. In accordance with the present invention, the metallic terminal or plate of the negative electrode is adequately covered with a thick felt pad, and iontophoretic burns are thereby avoided when a current time limitation is observed.

The nature of the thick felt electrode has been described. It is moistened for use by employing tap water. It has been found that distilled or deionized water may also be used.

In an illustrative example the palm of a hand was treated with a positive electrode having an area of 90 square centimeters. The negative electrode contacted the fingers and had an area of 30 square centimeters. The thickness of the felt was 6 millimeters.

A current of 15 milliamperes was allowable for a period of 10 minutes without an iontophoric burn occurring. Alternately, at 7.5 ma. the allowable treatment time was 20 minutes. At 3.75 ma. the allowable time was 40 minutes.

It has been determined that there is some particle or substance that migrates from metallic electrode 1 through intervenor 4 as current is caused to pass into skin 2. This particle or substance must not be allowed to fully migrate to the skin; for if it does, a burn results. Thus, the thickness of the intervenor acts as a transit barrier or delay to prevent the burn-causing particles from reaching the skin within the treatment period for a given current.

The intervenor cannot be conveniently rejuvenated, so as a practical matter the intervenors for the negative electrode are used as required for a treatment and then are disposed of.

The presently preferred type of intervenor material 4 is composed of metal-free natural fibers of wool or cotton.

Other equivalent man-made fiberous materials may be used, such as a synthetic of the viscose nylon or polyester type. Alternatively, porous materials such as foams or sponges may be used, and all of the recited substances have been generally termed "porous".

While the inhibition of perspiration is electrically induced, the inhibition does not occur immediately after treatment, but after an interval of about two weeks, after which time one or two further treatments will inaugurate another six week period, and so on.

The area of skin that is effectively treated also includes a leaching or spreading effect that extends beyond the immediate area that is directly contacted by the electrodes.

By empirical means it has been determined that the spreading of the electric current per se is very small in relation to the spreading of the inhibition of perspiration. It therefore appears that the inhibition is the result of a chemical effect that creates a keratin plug in each sweat duct.

Because of the spreading effect of the treatment to a limited area beyond the skin that is contacted by the electrodes, the latter may be flat, without regard to undulation of the skin, as upon the palms of the hand or the soles of the feet. In prior electrode art it is believed that this spreading effect was not observed, or was not appreciated, since all of the art that has been examined has not commented upon it.

The spacing between the pairs of electrodes in FIGS. 2 and 3 may be relatively close, so long as the current is prevented from going from one electrode to the other without passing through the skin; hence not accomplishing the method of this invention.

To maximize safety and convenience to the user, batteries may be used for current source 8. The voltage required varies according to the total resistance of the load circuit. A voltage of 45 volts is typical. A small battery having this total voltage is commercially available and is suitable, since the battery need only supply a current of a few milliamperes.

An advantage of the close-spaced electrodes in FIGS. 2 and 3 lies in the fact that the treatment current may be rapidly increased at the start of a treatment without an undesired sensation to the user.

It is desirable that the current be increased from zero or a low value at the start. With close-spaced electrodes the current may be increased to treatment amplitude in a fraction of a second.

With a distally removed electrode having a spacing of many centimeters and perhaps attachment to another member of the body, the current must be increased slowly. A certain procedure is for a careful operator or the user to turn a current-controlling potentiometer very slowly and steadily so that pain and shock will be avoided. However, the distally removed electrode mode of treatment is equally effective in burn protection.

Unless close electrode spacing is employed the current must be slowly decreased at the end of the treatment.

Although inhibition of perspiration was considered primarily accomplished at the positive electrode, inhibition to a lesser degree is accomplished at the negative electrode.

A basic period of treatment for anhidrosis, the inhibition of perspiration, is forty minutes. Initially, six treatments are given, preferably one every other day.

Extensive preparation of the skin before the electric treatments is not required. However, in order to assure consistent results it is desirable to swab the skin where the electrodes are to be applied with rubbing alcohol.

Figure 4:
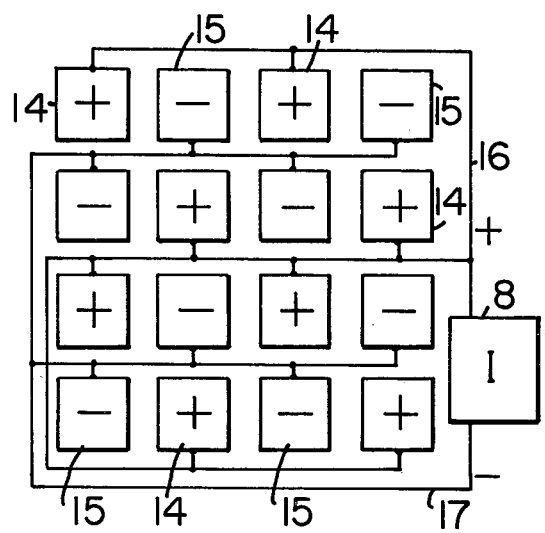
FIG. 4 is another alternate embodiment in which positive and negative electrodes of small size are spatially intermingled.

An opposite alternate structure to the distal arrangement of electrodes is that shown in FIG. 4. Here, small positive electrodes 14 and negative electrodes 15 are intermingled, being typically about one square centimeter in size and separated by a few millimeters one from the other. All are provided with a felt-like layer between the electrode proper and the skin. A system of conductors 16 for the positive and 17 for the negative electrodes which do not touch the skin connects all electrodes to current source 8.

Figure 5:
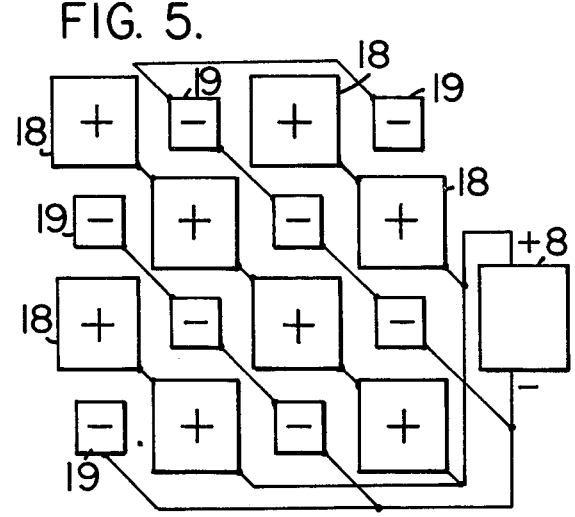
FIG. 5 is another alternate embodiment in which positive and negative electrodes of small size are spatially intermingled, with the positive electrodes larger than the negative electrodes.

Also, this type of intermingled structure may have the positive electrode 18 of larger area than that of the negative electrode 19, as shown in FIG. 5. The other aspects are the same as in FIG. 4.

When the positive electrode is made larger in area than that of the negative electrode in any of the embodiments, there is a limit to the difference in areas allowable in practice. This is about three-to-one, as evidenced by the 90 sq. cm. positive area and the 30 sq. cm. negative area electrodes in the embodiment of FIG. 3.

For simultaneous anti-perspiration treatment of two hands or two feet, two sets of electrodes according to FIG. 3 may be connected to a constant current source 8. However, we elect to use independent constant current sources, each powered by its own battery. This allows greater current for one hand than the other to compensate for possible different sensitivities of each hand.

We claim:

1. A method of applying electricity to a selected area of a living body while minimizing concomitant iontophoretic burn, said method including the steps of;
    applying a first electrode to the skin of said body at said selected area, with an electrically conductive, porous intervenor having a thickness very large in relation to the thickness of said skin, said intervenor interposed between said first electrode and said skin;
    applying a second electrode to said skin spaced from said first electrode; and
    applying direct current to said electrodes with a limitation on the amplitude of said direct current multiplied by the duration of applying said direct current, said limitation being proportional to the thickness of said intervenor associated with said first electrode.

2. A method as set forth in claim 1, further including the step of;
    dampening said intervenor associated with said first electrode with water to render it electrically conductive before it is applied to the skin of said body.

3. A method as set forth in claim 1 wherein:
    the second electrode is applied to said skin with a separation from the first electrode that is a small fraction of the linear extent of said electrodes; and
    the direct current is rapidly applied to said electrodes and skin within a time interval that is a very small fraction of the time interval employed for applying electricity.

4. A method as set forth in claim 1 further including the step of:
    interposing an electrically conductive, porous intervenor between said second electrode and said skin.

* * * * *